United States Patent
Kim et al.

(10) Patent No.: US 11,318,324 B2
(45) Date of Patent: May 3, 2022

(54) TREATMENT APPARATUS AND CONTROL METHOD FOR TREATMENT APPARATUS

(71) Applicant: LUTRONIC CORPORATION, Goyang (KR)

(72) Inventors: Won Joong Kim, Goyang (KR); Jae Yong Hong, Seoul (KR); Jong Tae Kim, Seoul (KR)

(73) Assignee: LUTRONIC CORPORATION, Goyang (KR)

( * ) Notice: Subject to any disclaimer, the term of this patent is extended or adjusted under 35 U.S.C. 154(b) by 280 days.

(21) Appl. No.: 15/743,262

(22) PCT Filed: Jul. 8, 2016

(86) PCT No.: PCT/KR2016/007412
§ 371 (c)(1),
(2) Date: Jan. 9, 2018

(87) PCT Pub. No.: WO2017/007272
PCT Pub. Date: Jan. 12, 2017

(65) Prior Publication Data
US 2018/0207444 A1    Jul. 26, 2018

(30) Foreign Application Priority Data

Jul. 9, 2015   (KR) .................. 10-2015-0097809

(51) Int. Cl.
*A61N 5/00*    (2006.01)
*A61N 5/06*    (2006.01)
*A61N 5/067*   (2006.01)

(52) U.S. Cl.
CPC .......... *A61N 5/0616* (2013.01); *A61N 5/067* (2021.08); *A61N 2005/007* (2013.01);
(Continued)

(58) Field of Classification Search
CPC ............ A61N 2005/007; A61N 5/0616; A61N 2005/0626; A61N 2005/063;
(Continued)

(56) References Cited

U.S. PATENT DOCUMENTS

| | | | |
|---|---|---|---|
| 6,514,278 B1* | 2/2003 | Hibst | .................. A61B 18/203 606/11 |
| 2008/0183110 A1* | 7/2008 | Davenport | ............... A61N 7/02 601/3 |

(Continued)

FOREIGN PATENT DOCUMENTS

| | | |
|---|---|---|
| EP | 0 827 716 A2 | 3/1998 |
| KR | 10-1998-0024312 A | 7/1998 |

(Continued)

OTHER PUBLICATIONS

International Search Report for PCT/KR2016/007412 filed on Jul. 8, 2016.

*Primary Examiner* — Rex R Holmes
*Assistant Examiner* — Sana Sahand (57) ABSTRACT

The present invention relates to a treatment apparatus and a control method for the treatment apparatus, and provides a treatment apparatus and a control method for the treatment apparatus, the treatment apparatus comprising: a treatment unit for transferring therapeutic energy at a preset period to a treatment position; a temperature measurement unit for measuring a temperature of the treatment position at a period different from the period at which the therapeutic energy is transferred; and a control unit for controlling an operation of the treatment unit on the basis of a result of measurement by the temperature measurement unit. The present invention enables a user to control a treatment content while accurately understanding the temperature of the treatment posi- (Continued)

tion, and thus can improve a treatment effect while preventing thermal damage to tissue.

14 Claims, 7 Drawing Sheets

(52) U.S. Cl.
CPC .............. *A61N 2005/063* (2013.01); *A61N 2005/0626* (2013.01); *A61N 2005/0659* (2013.01); *A61N 2005/0667* (2013.01)

(58) Field of Classification Search
CPC .... A61N 2005/0659; A61N 2005/0667; A61N 2005/067
See application file for complete search history.

(56) References Cited

U.S. PATENT DOCUMENTS

| | | |
|---|---|---|
| 2010/0121418 A1 | 5/2010 | Lee et al. |
| 2010/0249772 A1* | 9/2010 | Mehta .................. A61B 18/14 606/41 |
| 2012/0041523 A1* | 2/2012 | Solomon .............. A61N 5/0616 607/90 |
| 2012/0220999 A1* | 8/2012 | Long .................. A61B 18/1233 606/41 |
| 2013/0268031 A1* | 10/2013 | Ko ........................ A61N 5/0616 607/80 |
| 2013/0281851 A1* | 10/2013 | Carr ....................... A61N 5/025 600/435 |
| 2015/0157388 A1* | 6/2015 | Mehta ................... A61B 18/14 606/42 |
| 2016/0175610 A1* | 6/2016 | Livingston ............. G01J 1/429 607/94 |

FOREIGN PATENT DOCUMENTS

| | | | |
|---|---|---|---|
| KR | 10-0842040 B1 | | 6/2008 |
| KR | 10-1117198 B1 | | 3/2012 |
| KR | 10-2012-0108587 A | | 10/2012 |
| KR | 20120108587 A | * | 10/2012 |
| KR | 10-2013-0022309 A | | 3/2013 |
| KR | 10-1386137 B1 | | 4/2014 |
| KR | 10-2014-0079663 A | | 6/2014 |
| KR | 10-2015-0026704 A | | 3/2015 |
| WO | WO 2009/014312 A1 | | 1/2009 |
| WO | WO 2015/076584 A1 | | 5/2015 |

\* cited by examiner

TREATMENT APPARATUS AND CONTROL METHOD FOR TREATMENT APPARATUS

CROSS REFERENCE TO RELATED APPLICATIONS

This application is a U.S. National Stage of PCT/KR2016/007412, filed Jul. 8, 2016, which claims the priority benefit of Korean Patent Application No. 10-2015-0097809, filed on Jul. 9, 2015 in the Korean Intellectual Property Office, the disclosures of which are incorporated herein by reference.

TECHNICAL FIELD

The present invention relates to a treatment apparatus and a control method for the treatment apparatus and, more specifically, to a treatment apparatus employing a technique for preventing an excessive increase in the temperature of a treatment location and a control method for the treatment apparatus.

BACKGROUND ART

Recently, treatment techniques in which energy for treatment is transferred to the human body tissue to transform a state of the human body tissue or remove the transformed tissue have been widely applied. Therefore, treatment apparatuses that use various types of energy sources, such as laser, radio frequency (RF) wave, microwave, and ultrasound, are being developed.

Especially, as a treatment apparatus for treatment of skin lesions, an apparatus applying light energy as energy for treatment is widely used, and such an apparatus is also disclosed in Patent Registration No. 10-1269970. When light is irradiated to the skin tissue, the light penetrates into the skin and is absorbed into various tissues, such as collagen, hair follicles, and hemoglobin, located inside the skin according to the wavelength characteristics of the light. The absorbed light is converted into heat energy in the tissue to apply thermal damage to the corresponding tissue or transform the state of the tissue, thereby performing the treatment.

Here, the skin surface may be damaged by heat energy generated at the time of light irradiation. In order to prevent the damage, generally, the light is controlled to be irradiated with an output power at such an extent that the skin surface is not damaged or the skin surface is cooled before or during the irradiation of light.

However, since such a treatment manner is performed in a state in which the temperature of the skin surface is not known, thermal damage may occur depending on the skin characteristics of patients, and in some cases, the treatment may not be properly performed due to the non-transfer of sufficient energy.

DISCLOSURE

Technical Problem

An embodiment of the present invention provides a treatment apparatus capable of controlling the treatment scheme while checking the temperature of a treatment location during treatment and a control method for the treatment apparatus.

Technical Solution

According to an embodiment of the present invention, there is provided a treatment apparatus including: a treatment unit transferring energy for treatment to a treatment location at a predetermined period; a measurement unit measuring the temperature of the treatment location at a period different from the period at which the energy for treatment is transferred; and a control unit controlling the drive of the treatment unit on the basis of results measured by the temperature measurement unit.

Here, the period at which the temperature of the treatment location is measured by the temperature measurement unit may be shorter than the period at which the energy for treatment is delivered by the treatment unit, and more specifically, may be equal to or less than ⅓ the period at which the energy for treatment is transferred by the treatment unit. As one example, the temperature measurement unit may measure the temperature of the treatment location at a frequency of 30 Hz or higher.

Furthermore, the treatment unit may be configured to transfer energy to the treatment location by irradiating a treatment light, and more specifically, the treatment unit may irradiate a laser for treatment having a wavelength corresponding to an infrared or near-infrared region to the treatment location.

The temperature measurement unit may be disposed so as not to come into contact with the treatment location during treatment, and may measure the temperature by receiving a radiation light radiated from the treatment location.

Furthermore, the treatment apparatus may further include a filter filtering an interruption caused by the treatment light irradiated from the treatment unit while the temperature of the treatment location is measured by the temperature measurement unit.

The filter may exclude or correct temperature data, which contain an error due to the interruption by the treatment light, in temperature data of the treatment location, which are periodically obtained by the temperature measurement unit.

Here, in order to prevent the damage of a surface tissue at the treatment location, the control unit may stop the operation of the treatment unit or lower the amount of energy of treatment transferred by the treatment unit if the temperature of the treatment location is equal to or higher than a predetermined temperature.

Alternatively, the control unit may drive a cooling unit to cool the treatment location if the temperature of the treatment location is equal to or higher than the predetermined temperature.

According to another embodiment of the present invention, there is provided a control method for a treatment apparatus, the method including: irradiating a treatment light to a treatment location at a predetermined period; measuring the temperature of the treatment location at a period different from the period at which the treatment light is irradiated; and controlling a treatment mode on the basis of the temperature of the treatment location.

Advantageous Effects

According to the present invention, the treatment scheme can be controlled while the temperature of the treatment location is accurately checked, and thus a treatment effect can be improved while thermal damage to the tissue is prevented.

MODE FOR INVENTION

Hereinafter, preferred embodiments of the present invention will be described in detail with reference to the accompanying drawings. The following embodiment will be described by employing, as an example, a treatment apparatus for treating a skin lesion using a laser light. However, the present invention is not limited to the following embodiment, and it should be understood that the present invention can be applied to a treatment apparatus using various energy sources in addition to laser or a treatment apparatus for treating other lesions in addition to the skin lesion.

Figure 1:
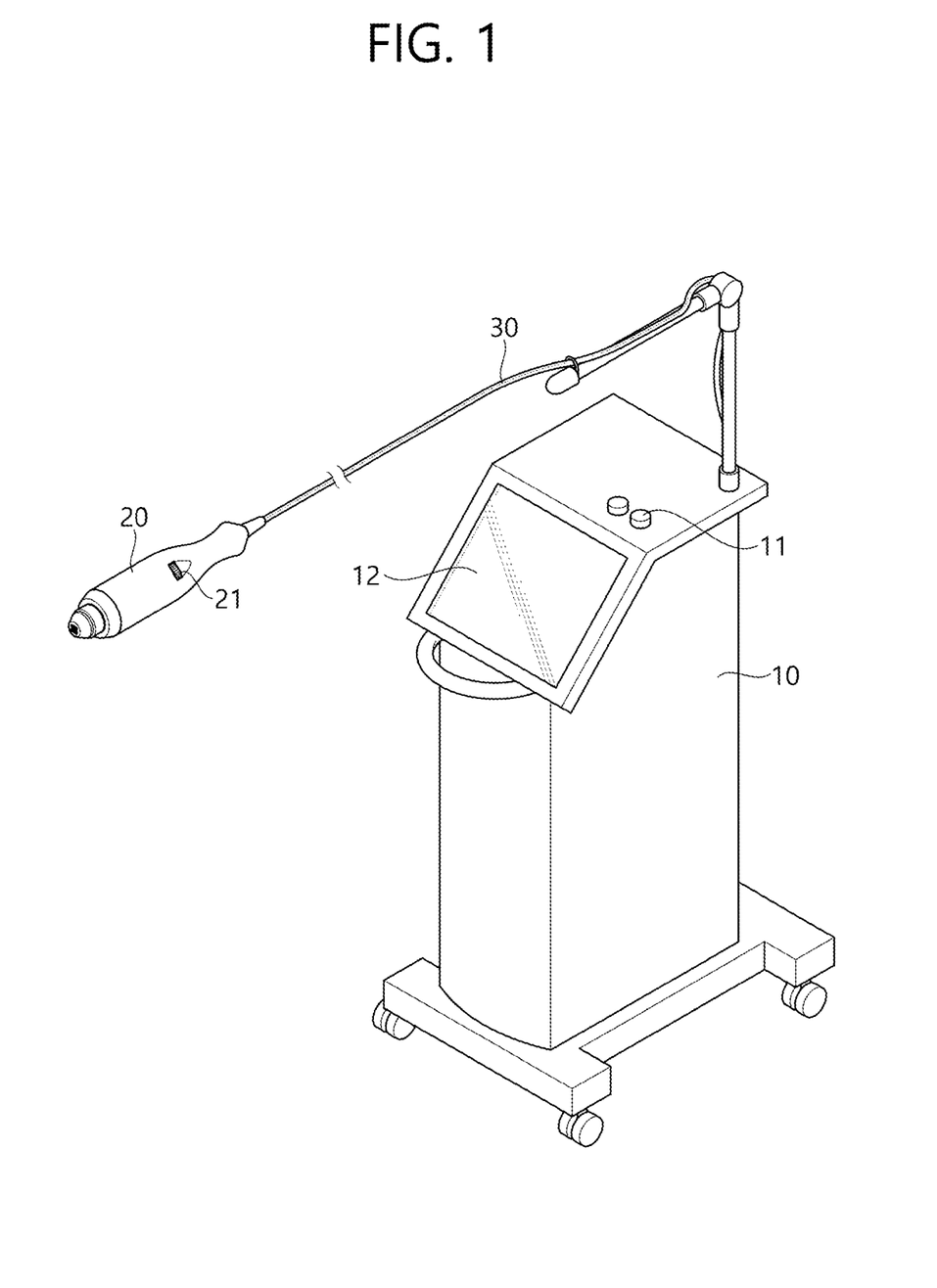
FIG. 1 is a diagram showing a treatment apparatus according to an embodiment of the present invention.
Figure 2:
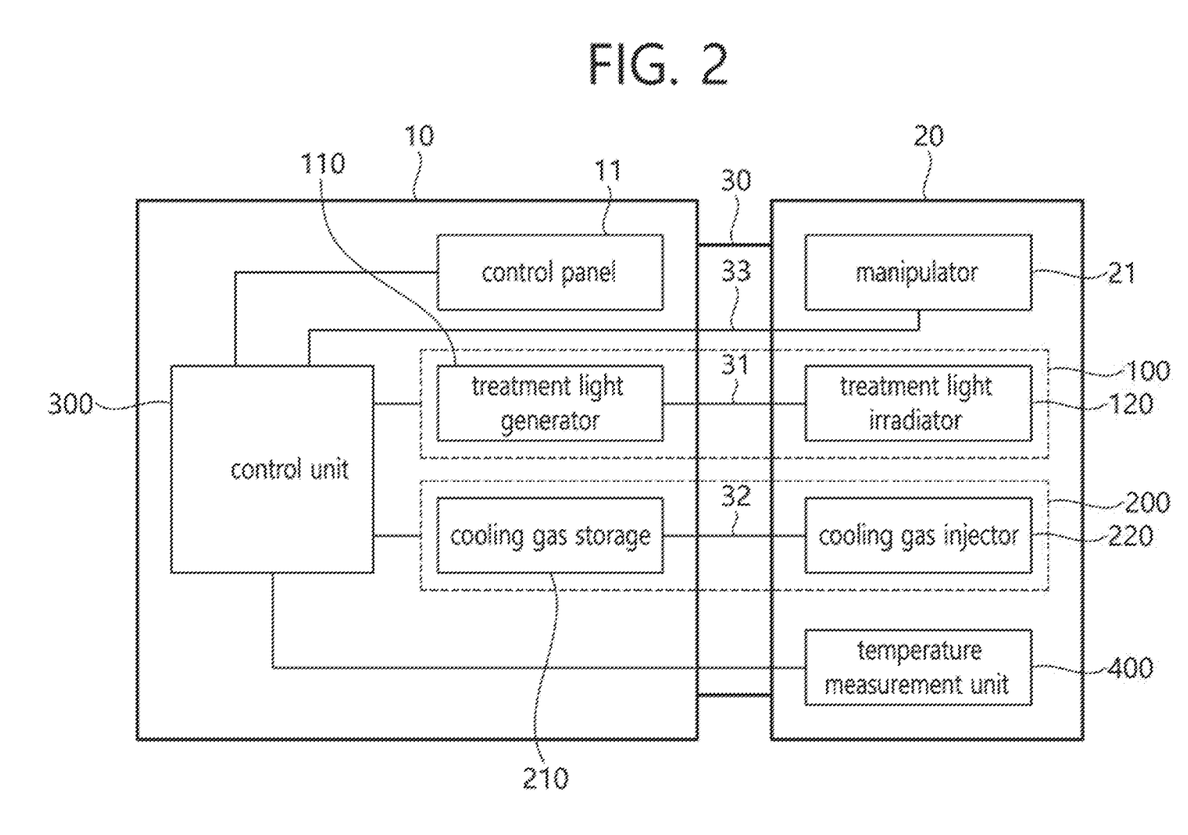
FIG. 2 is a diagram showing a connection relation of a main body and a handpiece in FIG. 1.

FIG. 1 is a diagram showing a treatment apparatus according to an embodiment of the present invention, and FIG. 2 is a diagram showing a connection relation of a main body and a handpiece in FIG. 1. As shown in FIG. 1, a treatment apparatus according to the present embodiment includes a main body 10, a handpiece 20, and a connector 30 connecting the main body 10 and the handpiece 20.

The main body 10 forms a main frame of the treatment apparatus, and various types of constituent elements are installed inside the main body 10. As shown in FIG. 2, a treatment light generator 110 of a treatment unit 100 and a cooling gas storage 210 of a cooling unit 200, each of which is to be described below, may be installed inside the main body. A control panel 11 capable of manipulating the treatment scheme and a display 12 for displaying various kinds of information to a user may be installed on an external surface of the main body 10.

The handpiece 20 is formed in a shape capable of being grasped by a user, and is configured to perform the treatment while the treatment location is easily changed during treatment. In the handpiece 20, a treatment light irradiator 120, a cooling gas injector 220, and a temperature measurement unit 400, each of which is to be described later, may be installed. A manipulator 21 capable of allowing the user to manipulate the drive of the handpiece during treatment may be formed on an external surface of the handpiece 20.

The connector 30 has a configuration of connecting the foregoing main body 10 and handpiece 20. The connector 30 may include an optical fiber 31 forming a light path from the treatment light generator 110 to the treatment light irradiator 120, a cooling channel 32 forming a travel path of cooling gas from the cooling gas storage 210 to the cooling gas injector 220, and a signal line 33 for transmitting various signals.

Hereinafter, the constituent elements respectively provided in the main body and the handpiece and the connection relations therebetween will be described with reference to FIG. 2.

For a start, the treatment unit 100 has a configuration of treating a patient by delivering energy of treatment to a treatment location. The treatment unit 100 may include: the treatment light generator 110 generating a treatment light; and a treatment light irradiator 120 irradiating the treatment light to the treatment location.

As shown in FIG. 2, the treatment light generator 110 is configured inside the main body. Here, the treatment light generator 110 may include a plurality of optical elements, such as a shutter, a mirror, and a lens, including a resonator. Therefore, the treatment light generator 110 may oscillate a laser from a laser medium of the resonator to allow the laser to be used as a treatment light. The treatment light generator 110 may be configured using various structures capable of generating a laser, and thus the specific description thereof will be omitted.

Meanwhile, one end of the treatment light generator 110 is connected with the treatment light irradiator 120 of the handpiece via a light carrier, such as an optical fiber. Therefore, the treatment light generated from the treatment light generator 110 is transmitted to the treatment light irradiator 120 of the handpiece through the optical fiber 31. The treatment light irradiator 120 constitutes a focusing optical system, and focuses the light transmitted from the optical fiber to irradiate the light to the treatment location.

The treatment unit 100 according to the present embodiment may use, as a treatment light, a light having a wavelength corresponding to an infrared or near-infrared region. Specifically, the treatment light may be a laser having a wavelength of equal to or more than 800 nm and equal to or less than 1100 nm. The treatment unit 100 generates the treatment light with such a wavelength into a pulse laser having a predetermined period and transmits the energy of treatment to the treatment location.

In the above description, the treatment unit 100 is divisionally provided into the main body 10 and the handpiece 20, but such a configuration merely corresponds to one embodiment, and thus can be variously modified. For example, both the treatment light generator 110 and the treatment light irradiator 120 may be configured in the handpiece 20, and the treatment unit 100 may be configured such that treatment is performed using other light energy but not a laser or using a different form of energy (for example, RF energy or ultrasonic energy), but not light.

Meanwhile, the cooling unit 200 is configured to cool the skin surface at the treatment location during treatment. Through the cooling unit 200, the thermal damage to the skin surface can be prevented. The cooling unit 200 includes a cooling gas storage 210 storing cooling gas and a cooling gas injector 220. As shown in FIG. 2, the cooling gas storage 210 is installed in the main body 10, and the cooling gas injector 220 is installed in the handpiece 20. The cooling gas storage 210 and the cooling gas injector 220 may be connected via the cooling channel of the connector 30.

In the present embodiment, cryogen gas that is evaporated at room temperature, such as HFC-134a, may be used as cooling gas. The cooling gas storage 210 stores the cooling gas in a high-pressure liquefied state, and may be detachably installed in the main body so as to be easily exchanged when the cooling gas is exhausted.

The cooling gas provided from the cooling gas storage 210 is provided to the handpiece 20 through the cooling channel. The cooling gas injector 220 of the handpiece is disposed adjacent to the treatment light irradiator 120 to inject the cooling gas to a location at which the treatment light is irradiated by the treatment light irradiator 120.

In the present embodiment, the cooling gas storage is detachably installed in the main body, but such a configuration merely corresponds to one example, and thus the present invention is not limited thereto. Besides, the cooling gas storage may be embedded in the main body and charged with the cooling gas, and the cooling gas storage may be installed directly in the handpiece, not in the main body.

Meanwhile, a control unit 300 controls the driving and operations of various constituent elements of the treatment apparatus. The control unit 300 can control the driving or not and operations of the treatment unit 100 and the cooling unit 200 according to the user input through the control panel 11 or the manipulator 21 or pre-stored conditions. Therefore, it is possible to control the irradiation or not, irradiation pattern, and output power intensity of the treatment light; the injection or not, injection pattern, and injection pressure of the cooling gas; and the like, and therefore, various schemes of treatment can be performed.

As described above, the treatment unit 100 delivers energy to the treatment location to perform the treatment. However, the human tissue is thermally damaged if the human tissue is heated at a temperature exceeding a reference temperature, and thus the treatment location may be damaged when excessive energy is transferred through the treatment unit 100. Conversely, if the irradiation of the treatment light is stopped or the treatment location is cooled in a state in which sufficient energy is not delivered to the treatment location, the treatment may not be properly performed.

Therefore, the treatment apparatus according to the present embodiment may further include a temperature measurement unit 400. The temperature measurement unit 400 may measure the surface temperature of the treatment location in real time. In addition, the control unit 300 controls the operation of the treatment unit 100 and/or the cooling unit 200 in real-time in consideration of the surface temperate of the treatment location, measured by the temperature measurement unit 400. Therefore, the treatment apparatus according to the present invention can perform the treatment while preventing the thermal damage to the treatment location and providing the optimal treatment effect.

Figure 3:
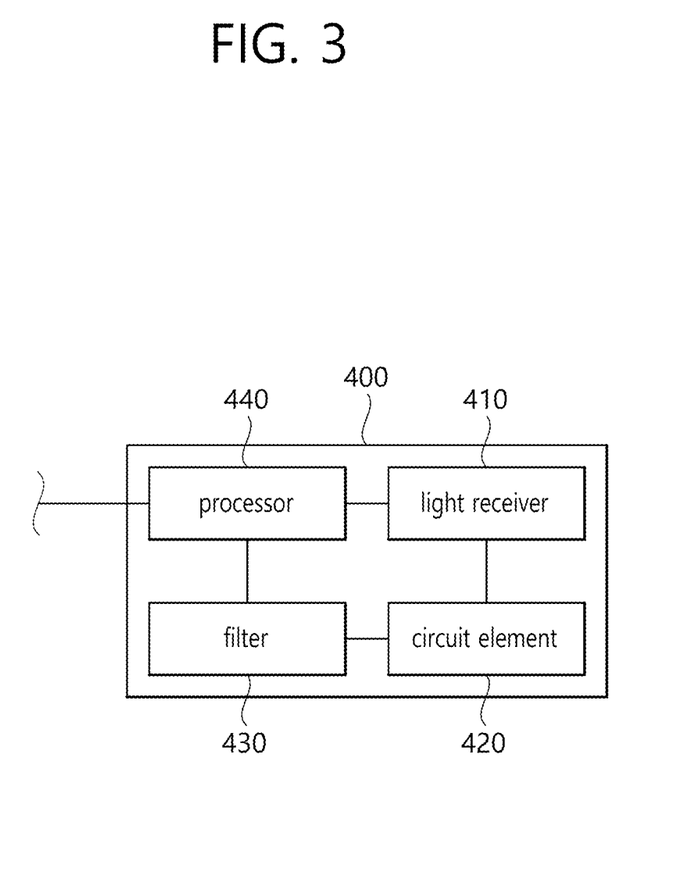
FIG. 3 is a block diagram showing a configuration of a temperature measurement unit in FIG. 2.

FIG. 3 is a block diagram showing a configuration of the temperature measurement unit in FIG. 2. Hereinafter, the configuration of the temperature measurement unit will be described in more detail with reference to FIG. 3.

The temperature measurement unit 400 according to the present embodiment is provided in the handpiece 20, and includes a light receiver 410 for receiving a radiation light radiated from the treatment location. The infrared radiation energy radiated from a particular object depends on the temperature of the object. Therefore, the temperature measurement unit 400 can measure the temperature of the treatment location by receiving the radiation light in an infrared region radiated from the treatment location.

The light receiver 400 is disposed adjacent to an end portion of the handpiece 20, and is installed so as not to come into contact with the treatment location during treatment. The use of a contact type sensor makes it difficult to check the temperature of a location to which the treatment light is irradiated, but in the present embodiment, the temperature is measured in a non-contact manner, so that the temperature of the treatment location can be measured using the treatment light even while the treatment is ongoing.

The light receiver 410 may include an element for converting an infrared ray into an electrical signal when receiving the infrared ray. In addition, it is preferable to use, as the light receiver 410, a device that has a sensing response time (time required for extinction of the previously measured information) of 50 ms or less so as to measure the temperature at a rapid period. Here, the light receiver 400 may further include a lens (not shown) for focusing the received light or a filter (not shown) for filtering only the light in a particular wavelength band.

The electric signal obtained from the light receiver 410 is transmitted to a circuit element 420. The circuit element 420 processes the electric signal obtained from the light receiver 410. For example, the circuit element 420 may include an amplification circuit (not shown) for amplifying an electric signal and a linear circuit (not shown) for linearly converting an electric signal according to the temperature distribution. However, such a configuration of the circuit element merely corresponds to one example, and besides, the circuit element may be, of course, variously configured as needed.

Meanwhile, the processor 440 of the temperature measurement unit 400 may control the operation of the light receiver 410 and measure the temperature of the treatment location from the signal transmitted through the light receiver 410 and the circuit element 420. The processor 440 may be operated by a signal of the control unit 300 of the main body, and transmit the measured temperature information of the treatment location to the control unit 300 of the main body. FIG. 3 shows that the temperature measurement unit 400 includes a separate processor 440, but such a configuration merely corresponds to one example, and thus the operation of the foregoing microprocessor may be performed by the foregoing control unit of the main body.

Meanwhile, the temperature measurement unit 400 measures the temperature by receiving the radiation light radiated from the treatment location, and thus the temperature value may be inaccurately measured by an interruption of the treatment light in a state in which the treatment light is irradiated. The treatment light is irradiated to the treatment location, and a portion of the treatment light is absorbed and a portion of the treatment light is reflected or scattered from the treatment location. Therefore, if the treatment light is irradiated at a time point adjacent to a time point at which the light receiver 410 receives the radiation light, the treatment light as well as the radiation light are received by the light receiver, causing an error. Especially, if the treatment light and the irradiation light have similar wavelengths as in the present embodiment, such an error is highly likely to occur. Therefore, the temperature measurement unit 400 may adopt various techniques so as to measure the temperature of the treatment location during treatment, despite such an error.

In one technique, the temperature measurement unit may measure the temperature of the treatment location by receiving the radiation light at a time point at which the treatment light is not irradiated. In this case, the time point at which the radiation light is received is different from the time point at which the treatment light is irradiated, and thus an interference phenomenon due to the treatment light can be prevented at the time of temperature measurement. In this case, it is preferable that one controller controls the operation time points of the treatment light irradiator and receiver, but the treatment light irradiator and receiver are difficult to control if they are controlled by separate processors or controllers.

In another technique, which is employed in the present embodiment, the temperature measurement unit 400 may measure the temperature of the treatment location at a period shorter than the period at which the treatment light is irradiated. In addition, the data containing an error due to an interference of the treatment light is filtered from the measured information, and then the temperature of the treatment location can be detected on the basis of the remaining data.

Figure 4A:
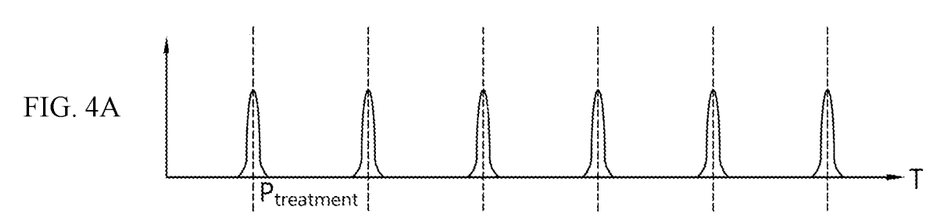
FIGS. 4A to 4D depict graphs showing examples of measurement data according to the treatment light period and the temperature measurement period.
Figure 4B:
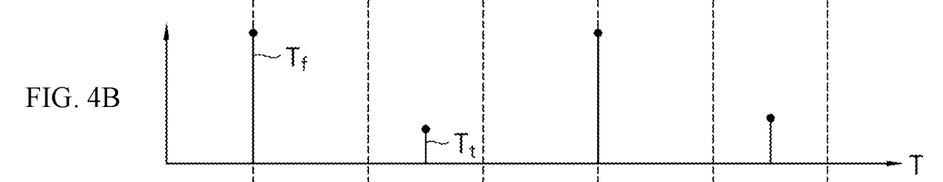
Figure 4C:
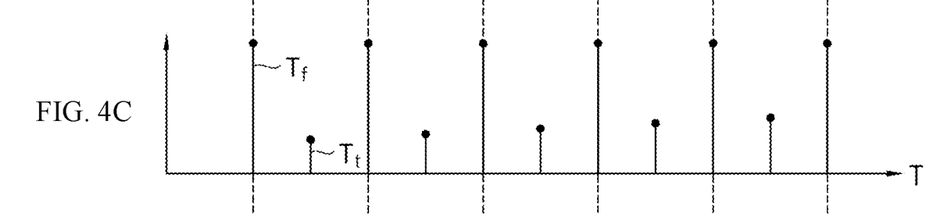
Figure 4D:
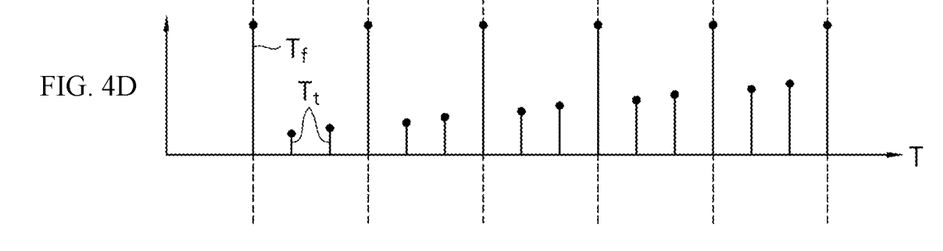

FIGS. 4A to 4D provide graphs showing examples of measurement data according to the treatment light irradiation period and the temperature measurement period. Specifically, FIG. 4A is a graph showing an irradiation pattern of the treatment light; FIG. 4B illustrates a case where the temperature measurement period is 1.5 times the treatment light irradiation period; FIG. 4C illustrates a case where the temperature measurement period is ½ the treatment light irradiation period; and FIG. 4D illustrates a case where the temperature measurement period is ⅓ the treatment light irradiation period. For convenience of explanation, the initial temperature measurement time point is allowed to coincide with the time point at which the irradiation light is irradiated.

As shown in FIGS. 4A to 4D, the temperature measurement unit 400 measures the temperature of the treatment location at a predetermined period, and it can be seen that the temperature measured at a time point adjacent to the time point at which the treatment light is irradiated is rapidly increased. This indicates an error due to an interference of the reflected or scattered treatment light as described above, rather than a substantial temperature increase of the treatment location at the time point at which the treatment light is irradiated.

Here, in FIGS. 4B and 4C, the values ($T_t$) obtained by the normal temperature measurement and the values ($T_f$) containing an error due to an interference of the treatment light are alternatively detected, and thus it may be difficult to determine which data between these values have a normal value. Certainly, in cases where the periods are not exactly an integer multiple or the phase is somewhat changed unlike FIGS. 4B and 4C, the normal measurement value ($T_t$) and the error-containing value ($T_f$) are not always measured alternately, but that the normal measurement value ($T_t$) and the error-containing value ($T_f$) may be alternately measured in a certain section.

Whereas, when the temperature measurement period is ⅓ the treatment light irradiation period as shown in FIG. 4D, the number of normal measurement values ($T_t$) is more than the number of error-containing values ($T_f$) among three types of measurement values and the two types of values are not alternatively measured, and thus the error-containing values ($T_f$) can be easily identified.

Therefore, the processor 440 of the temperature measurement unit 400 according to the present embodiment can control the light receiver 410 so as to measure the time at a period, which is less than ⅓ times the period at which the treatment light is irradiated. In this case, the temperature measurement is performed two or more times between the two sequential irradiation events of the treatment light in any section, and therefore, the error-containing value ($T_f$) can be easily identified.

Figure 5:
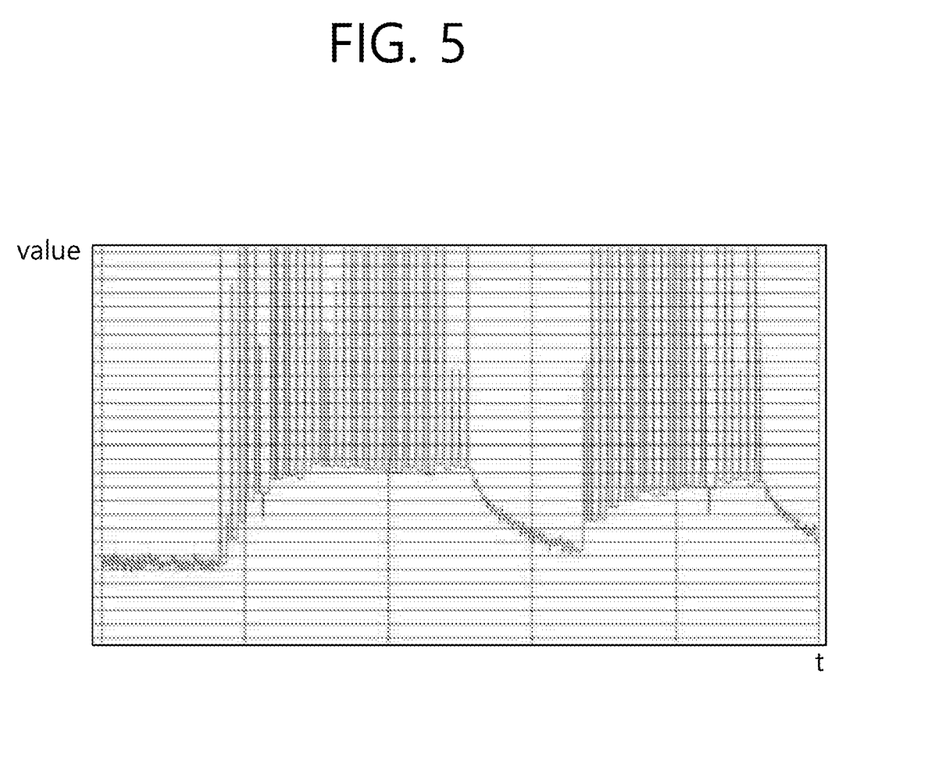
FIG. 5 is a graph showing the measurement values before filtration in FIG. 3.
Figure 6:
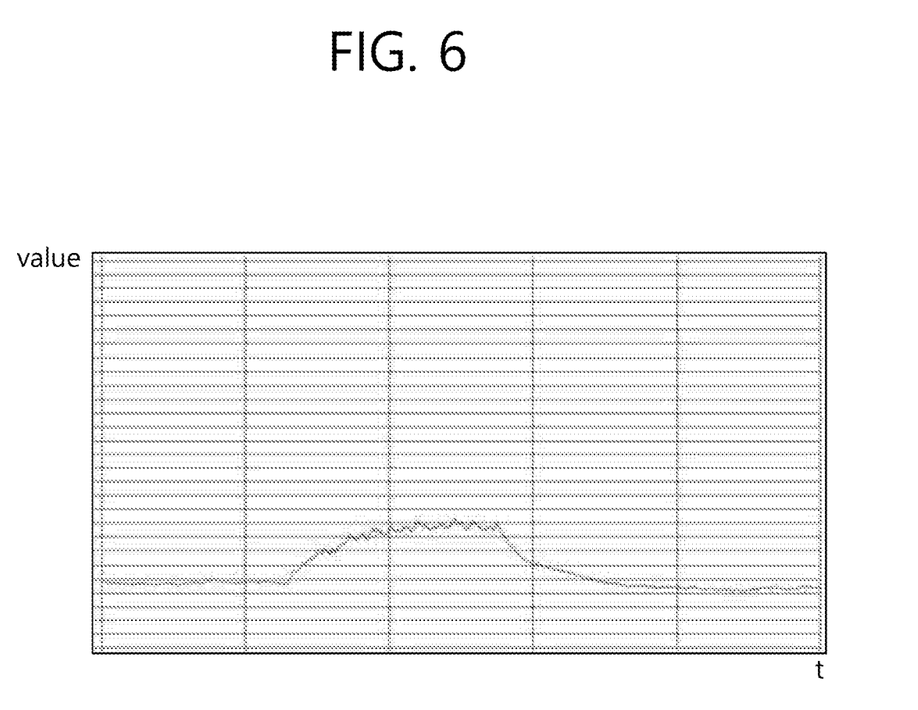
FIG. 6 is a graph showing the measurement values obtained by filtration by a filter in FIG. 5.

FIG. 5 shows error-containing values intactly without separate filtration, and FIG. 6 shows the values after the correction of the error-containing values through filtration by the filter 430. According to the temperature measurement unit 400 of the present embodiment, even though the measurement data have an error due to an interference of the treatment light, the temperature of the treatment location can be monitored more accurately by the filter 430 filtering the error-containing data.

The filter 430 may be designed in various manners. As one example, the filter may determine the transmitted data as having an error-containing value if the transmitted data has an increase or decrease exceeding a reference value when compared with a tendency of a plurality of previously transmitted data. If the transmitted data is determined as having an error-containing value, the measurement value may be adjusted by removing the error-containing value or replacing the error-containing value with a previously measured data value. Besides, the filter may be designed to filter data in various manners.

As such, the filtered data are transmitted to the processor 440 of the temperature measurement unit, and the processor 440 can transmit the measured temperature of the treatment location to the control unit 300 in real time. Therefore, the control unit 300 may control the treatment unit 100 or the cooling unit 200 considering the real-time measured temperature of the treatment location, and may transmit the temperature of the treatment location to the user through the display 12.

It has been described that the foregoing temperature measurement unit 400 includes the light receiver 410, the circuit element 420, the filter 430, and the processor 440, but these are divisionally provided for convenience of explanation, and the respective constituent elements are not necessarily configured as separate elements and components. For example, the circuit element and the filter are not configured as separate elements, but may be implemented in a single circuit element including a filter circuit. Alternatively, the filter and the processor may not be configured as separate elements, but may be configured to process an operation of filtering an error-containing data in processing an electrical signal transmitted from the processor. It should be understood that the constituent elements shown in FIG. 3 are separately configured based on the functions thereof, and may be implemented in various manners.

The treatment apparatus capable of measuring the temperature of the treatment location in real time using the temperature measuring unit 400 and reflecting the temperature data on the control operation has been described above. In the foregoing embodiment, the temperature measurement unit has been set such that the temperature measurement period is less than ⅓ the treatment light irradiation period, but the present invention is not limited thereto.

For example, the temperature measurement period and the treatment light irradiation period are set to be different from each other, so that the temperature measurement and the treatment light irradiation are not performed at the same time point. Alternatively, any one of the temperature measurement period and the treatment light irradiation period is set to be an integral multiple of the other and the time point of the temperature measurement and the time point of the treatment light irradiation are set to have a predetermined time interval, so that the temperature measurement and the treatment light irradiation are not performed at the same time (the time interval is set to be different from the temperature measurement period or the treatment light irradiation period).

As another example, the temperature measurement period may be set to be equal to or less than one time the treatment light irradiation period, and then it may be determined whether the data has an error containing value in consideration of the increase and decrease ratio compared with the previous data. Furthermore, the process can control the phase or timing of temperature measurement if the number of error-containing data in the measured data is large.

As described above, the present invention is not limited to the above-described embodiments, and may be implemented through various design and modification.

Figure 7:
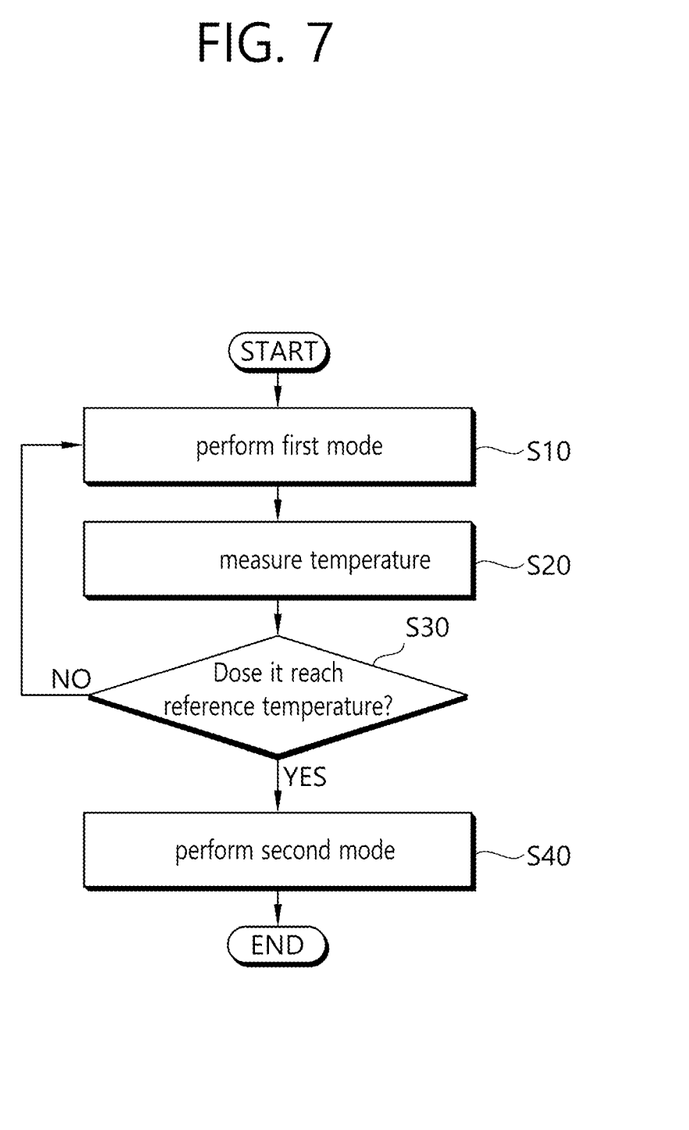
FIG. 7 is a flowchart showing a control method for the treatment apparatus in FIG. 1.

FIG. 7 is a flowchart showing a control method for the treatment apparatus in FIG. 1. Hereinafter, a control method for the treatment apparatus according to the above-described embodiment will be specifically described with reference to FIG. 7.

If the treatment location and treatment scheme corresponding to a lesion of a patient is determined, a user locates a handpiece 20 to the treatment location, and then a step of driving the treatment apparatus in a first mode may be performed (S10). Here, the first mode is a stage in which the treatment is performed by irradiating the treatment light to the treatment location, and the first mode may be input by the user or recommended by the treatment apparatus corresponding to the lesion of the patient. While the present step is performed, the treatment apparatus can deliver the energy of treatment to the treatment location by irradiating the treatment light at a predetermined first period.

Meanwhile, while the treatment is performed in the first mode, a step of measuring the temperature of the treatment location may be performed by the temperature measurement unit 400 (S20). The measurement of the temperature of the treatment location is performed in a manner of receiving the radiation light radiated from the treatment location and then measuring the temperature of the treatment location from the radiation light. The present step has been shown to be performed after the step of performing the first mode in FIG. 7, but is merely an initiation time point for each step. While the treatment apparatus is operated in the first mode, the treatment apparatus is controlled to continuously perform the temperature measurement.

In the present step, the temperature measurement is performed at a second period different from a first period, which corresponds to the treatment light irradiation period, and more specifically, the treatment apparatus may be operated such that the second period is controlled to be less than ⅓ the first period.

As described above, the treatment operation and the temperature measurement are performed at the same time, and thus an error may occur due to an interference due to the treatment light in the temperature measurement. Therefore, the temperature measurement is performed two or more times between the two adjacent irradiation events of the treatment light, and therefore, so that the data containing an error due to the interference can be easily identified.

The present step further comprises a step of filtering the data obtained from the received radiation light by the filter 430. The filter 430 filters the data containing an error due to an interference of the treatment light, so that the temperature of the treatment location can be accurately monitored using the remaining data.

While the temperature of the treatment location is measured through the above-described steps, a control unit 300 determines whether the temperature of the treatment location reaches a predetermined reference temperature (S30). The control unit switches the operation mode of the treatment apparatus to the second mode if the temperature of the treatment location is determined to reach the reference temperature, and the above-described steps may be repeated until the temperature of the treatment location reaches the reference temperature if the temperature of the treatment location is not determined to reach the reference temperature.

As such, the reference temperature is a temperature as a criterion for switching the first mode into the second mode. Here, the reference temperature may be a temperature at which thermal damage of the skin occurs. The treatment apparatus according to the present embodiment transfers energy to the treatment location to perform the treatment, but the treatment location is damaged when excessive energy is transferred. Therefore, in the present embodiment, the reference temperature is set to a temperature in the range of 45-55° C., which may be a criterion for thermal damage, and thus, if the temperature of the treatment location reaches the reference temperature, the operation mode can be switched to the second mode in which a smaller amount of energy is transferred compared with the first mode.

As one example, the second mode may be a mode in which the irradiation of the treatment light from the treatment unit is stopped immediately or after a predetermined time. Alternatively, the second mode may be a mode in which the treatment light with a lower output power compared with the first mode is irradiated. Furthermore, the second mode may include a mode in which the cooling unit is operated to cool the treatment location. In addition, the second mode may be operated in various manners such that a smaller amount of energy is delivered to the treatment location compared with the first mode.

Meanwhile, the reference temperature may be a temperature at which thermal damage occurs in the above description, but besides, the reference temperature may be set for various purposes. For example, if the skin treatment scheme is set such that a first treatment is performed in the first mode and then a second treatment is performed in the second mode, it is determined whether the first treatment is completed based on whether the temperature reaches the predetermined set temperature, and then it is determined the time point at which the second treatment is performed.

As such, the treatment apparatus according to the present invention is configured such that the treatment is performed while the temperature of the treatment location is monitored in real time during treatment, and thus the thermal damage of the treatment location can be prevented and the optimized treatment can be performed.

Particularly, even though an interference occurs by the treatment light due to the treatment light when the temperature of the treatment location is detected, the temperature can be accurately measured using temperature measurement patterns and filtering techniques, thereby minimizing errors that may occur due to the temperature measurement error.

Although the embodiment of the present invention has been described in detail, the present invention is not limited to the above embodiment. It should be understood that the present invention may be embodied with various changes and modifications without departing from the scope of the invention as defined in the appended claims by any person skilled in the art to which the present invention belongs.

The invention claimed is:

1. A treatment apparatus comprising:
  a treatment unit periodically transferring energy for treatment by irradiating a treatment light to a treatment location with a first period;
  a temperature measurement unit, by receiving a radiation light radiated from the treatment location, periodically measuring the temperature of the treatment location with a second period different from the first period with which the energy for treatment is transferred; and
  a control unit controlling the irradiation of the treatment light from the treatment unit on the basis of results measured by the temperature measurement unit,
  wherein the first period is a time interval between two sequential irradiation events of the treatment light, the second period is a time interval between two sequential measurements of the temperature of the treatment location, the second period is shorter than the first period, the second period has a substantially constant value, and the second period is greater than 0 and less than ⅓ of the first period, and wherein the temperature measurement unit periodically measures the temperature of the treatment location with the second period, regardless of a timing to irradiate the treatment light.

2. The treatment apparatus of claim 1, wherein the treatment light comprises a laser.

3. The treatment apparatus of claim 1, wherein the treatment light comprises a light having a wavelength corresponding to an infrared or near-infrared region.

4. The treatment apparatus of claim 1, wherein the temperature measurement unit is disposed so as not to come into contact with the treatment location during treatment.

5. The treatment apparatus of claim 1, further comprising a filter filtering an interruption caused by the treatment light irradiated from the treatment unit while the temperature of the treatment location is measured by the temperature measurement unit.

6. The treatment apparatus of claim 5, wherein the filter excludes or corrects temperature data, which contain an error due to the interruption by the treatment light, in temperature data of the treatment location, which are periodically obtained by the temperature measurement unit, by removing the error.

7. The treatment apparatus of claim 1, wherein, in order to prevent damage of a surface tissue at the treatment location, the control unit stops an operation of the treatment unit or lowers an amount of energy of treatment transferred by the treatment unit if the temperature of the treatment location is equal to or higher than a predetermined temperature.

8. The treatment apparatus of claim 7, wherein the control unit drives a cooling unit to cool the treatment location if the temperature of the treatment location is equal to or higher than the predetermined temperature.

9. The treatment apparatus of claim 1, wherein the control unit controls one or more of whether to irradiate the treatment light or not, an irradiation pattern of the treatment light, and output power intensity of the treatment light.

10. The treatment apparatus of claim 1, wherein the first period and the second period are respectively predetermined.

11. The treatment apparatus of claim 1, wherein the first period is between a first time and a second time at which the energy for treatment is sequentially transferred by the treatment unit, and the second period is between a third time and a fourth time at which the temperature of the treatment location is sequentially measured by the temperature measurement unit.

12. A control method for a treatment apparatus, the method comprising:

irradiating a treatment light to a treatment location periodically with a first period, by a treatment unit, to transfer energy for treatment to the treatment location;

measuring a temperature of the treatment location periodically with a second period different from the first period with which the treatment light is irradiated; and controlling a treatment mode on the basis of the temperature of the treatment location, wherein the first period is a time interval between two sequential irradiation events of the treatment light, the second period is a time interval between two sequential measurements of the temperature of the treatment location, the second period is shorter than the first period, the second period has a substantially constant value, and the second period is greater than 0 and less than $\frac{1}{3}$ of the first period, and wherein the temperature of the treatment location is measured periodically with the second period, regardless of a timing to irradiate the treatment light.

13. The method of claim 12, further comprising determining data as having an error-containing value by comparing a value of the data with a reference value and filtering the determined data as having the error-containing value occurring due to an interruption by the treatment light during the measurement of the temperature, wherein in the step for measuring the temperature of the site of temperature, the temperature of the treatment location is measured by receiving a radiation light radiated from the treatment location.

14. The method of claim 12, wherein the control unit restricts an operation of the treatment unit or drives a cooling unit to cool the treatment location if the temperature of the treatment location is determined to be equal to or higher than the predetermined value.

* * * * *